United States Patent
Masel et al.

(10) Patent No.: US 10,428,432 B2
(45) Date of Patent: Oct. 1, 2019

(54) CATALYST LAYERS AND ELECTROLYZERS

(71) Applicant: Dioxide Materials, Inc., Boca Raton, FL (US)

(72) Inventors: Richard I. Masel, Boca Raton, FL (US); Zengcai Liu, Boca Raton, FL (US); Robert Kutz, Boca Raton, FL (US); Syed Dawar Sajjad, Boca Raton, FL (US)

(73) Assignee: Dioxide Materials, Inc., Boca Raton, FL (US)

( * ) Notice: Subject to any disclaimer, the term of this patent is extended or adjusted under 35 U.S.C. 154(b) by 0 days.

(21) Appl. No.: 15/908,325

(22) Filed: Feb. 28, 2018

(65) Prior Publication Data

US 2019/0071788 A1    Mar. 7, 2019

Related U.S. Application Data

(60) Division of application No. 15/158,227, filed on May 18, 2016, now Pat. No. 9,945,040, which is a
(Continued)

(51) Int. Cl.
*H01M 8/00* (2016.01)
*C25B 11/04* (2006.01)
(Continued)

(52) U.S. Cl.
CPC .......... *C25B 11/0489* (2013.01); *C02F 1/461* (2013.01); *C25B 1/00* (2013.01);
(Continued)

(58) Field of Classification Search
CPC ................................. B29C 41/50; H01M 8/10
See application file for complete search history.

(56) References Cited

U.S. PATENT DOCUMENTS 3,401,099 A    9/1968   McEvoy
3,779,883 A   12/1973   Heit
(Continued)

FOREIGN PATENT DOCUMENTS

EP    0151510 A1    8/1985
JP    H02166128 A   6/1990
(Continued)

OTHER PUBLICATIONS

Chen, W.; Zhang, Y.; Zhu, L.; Lan, J.; Xie, R.; You, J. J. Am. Chem. Soc. 2007, 129, 13879-13886. (Year: 2007).*
(Continued)

*Primary Examiner* — Rip A Lee
(74) *Attorney, Agent, or Firm* — Corridor Law Group, P.C.

(57) ABSTRACT

A catalyst layer for an electrochemical device comprises a catalytically active element and an ion conducting polymer. The ion conducting polymer comprises positively charged cyclic amine groups. The ion conducting polymer comprises at least one of an imidazolium, a pyridinium, a pyrazolium, a pyrrolidinium, a pyrrolium, a pyrimidium, a piperidinium, an indolium, a triazinium, and polymers thereof. The catalytically active element comprises at least one of V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Tl, Pb, Bi, Sb, Te, U, Sm, Tb, La, Ce and Nd. In an electrolyzer comprising the present catalyst layer, the feed to the electrolyzer comprises at least one of $CO_2$ and $H_2O$.

14 Claims, 4 Drawing Sheets

Related U.S. Application Data continuation-in-part of application No. 15/090,477, filed on Apr. 4, 2016, now Pat. No. 9,580,824, which is a continuation-in-part of application No. 14/704,935, filed on May 5, 2015, now Pat. No. 9,370,773, which is a continuation-in-part of application No. PCT/US2015/026507, filed on Apr. 17, 2015, and a continuation-in-part of application No. PCT/US2015/014328, filed on Feb. 3, 2015, said application No. 15/158,227 is a continuation-in-part of application No. 14/704,934, filed on May 5, 2015, now Pat. No. 9,481,939, which is a continuation-in-part of application No. PCT/US2015/026507, filed on Apr. 17, 2015, and a continuation-in-part of application No. PCT/US2015/014328, filed on Feb. 3, 2015, said application No. 15/158,227 is a continuation-in-part of application No. PCT/US2015/014328, filed on Feb. 3, 2015, and a continuation-in-part of application No. PCT/US2015/026507, filed on Apr. 17, 2015.

(60) Provisional application No. 62/066,823, filed on Oct. 21, 2014.

(51) Int. Cl.

| | | |
|---|---|---|
| *G01N 27/333* | (2006.01) | |
| *H01M 4/90* | (2006.01) | |
| *C02F 1/461* | (2006.01) | |
| *C25B 13/08* | (2006.01) | |
| *C25B 3/04* | (2006.01) | |
| *C25B 9/10* | (2006.01) | |
| *H01M 8/1023* | (2016.01) | |
| *H01M 8/1044* | (2016.01) | |
| *H01M 4/86* | (2006.01) | |
| *C25B 1/00* | (2006.01) | |

(52) U.S. Cl.
CPC .................. *C25B 3/04* (2013.01); *C25B 9/10* (2013.01); *C25B 11/0405* (2013.01); *C25B 13/08* (2013.01); *G01N 27/3335* (2013.01); *H01M 4/8668* (2013.01); *H01M 4/9041* (2013.01); *H01M 4/9083* (2013.01); *H01M 8/1023* (2013.01); *H01M 8/1044* (2013.01)

(56) References Cited

U.S. PATENT DOCUMENTS

| | | | |
|---|---|---|---|
| 3,896,015 A | | 7/1975 | McRae |
| 4,113,922 A | | 9/1978 | D'Agostino et al. |
| 4,430,445 A | | 2/1984 | Miyake et al. |
| 4,456,521 A | | 6/1984 | Solomon et al. |
| 4,523,981 A | | 6/1985 | Ang et al. |
| 4,673,473 A | | 6/1987 | Ang et al. |
| 4,921,585 A | | 5/1990 | Molter |
| 5,883,762 A | | 3/1999 | Calhoun et al. |
| 5,997,715 A | * | 12/1999 | Roberts ................ C07D 301/14 205/428 |
| 7,704,369 B2 | | 4/2010 | Olah et al. |
| 7,931,824 B2 | | 4/2011 | Gin et al. |
| 8,138,380 B2 | | 3/2012 | Olah et al. |
| 8,313,634 B2 | | 11/2012 | Bocarsly et al. |
| 8,357,270 B2 | | 1/2013 | Gilliam et al. |
| 8,414,758 B2 | | 4/2013 | Deguchi et al. |
| 8,449,652 B2 | | 5/2013 | Radosz et al. |
| 8,500,987 B2 | | 8/2013 | Teamey et al. |
| 8,524,066 B2 | | 9/2013 | Sivasankar et al. |
| 8,552,130 B2 | | 10/2013 | Lewandowski et al. |
| 8,562,811 B2 | | 10/2013 | Sivasankar et al. |
| 8,568,581 B2 | | 10/2013 | Sivasankar et al. |
| 8,592,633 B2 | | 11/2013 | Cole et al. |
| 8,658,016 B2 | | 2/2014 | Lakkaraju et al. |
| 8,663,447 B2 | | 3/2014 | Bocarsly et al. |
| 8,696,883 B2 | | 4/2014 | Yotsuhashi et al. |
| 8,721,866 B2 | | 5/2014 | Sivasankar et al. |
| 9,012,345 B2 | | 4/2015 | Masel et al. |
| 9,255,335 B2 | | 2/2016 | Kanan et al. |
| 9,370,773 B2 | * | 6/2016 | Masel ................... B01J 41/14 |
| 9,481,939 B2 | * | 11/2016 | Masel ................... B01J 41/14 |
| 9,580,824 B2 | * | 2/2017 | Masel ................... C25B 13/08 |
| 9,849,450 B2 | * | 12/2017 | Masel ................... C25B 1/10 |
| 9,943,841 B2 | * | 4/2018 | Masel ................... C02F 1/461 |
| 9,945,040 B2 | * | 4/2018 | Masel ................... C02F 1/461 |
| 9,982,353 B2 | * | 5/2018 | Masel ................... C02F 1/461 |
| 10,047,446 B2 | * | 8/2018 | Kaczur ................. C25B 1/00 |
| 2007/0259236 A1 | | 11/2007 | Lang et al. |
| 2009/0014336 A1 | | 1/2009 | Olah et al. |
| 2009/0266230 A1 | | 10/2009 | Radosz et al. |
| 2011/0114502 A1 | | 5/2011 | Cole et al. |
| 2011/0201847 A1 | | 8/2011 | Wolk et al. |
| 2011/0237830 A1 | | 9/2011 | Masel |
| 2012/0171583 A1 | * | 7/2012 | Bocarsly ............. H01M 4/8657 429/413 |
| 2012/0186446 A1 | | 7/2012 | Bara et al. |
| 2012/0247969 A1 | | 10/2012 | Bocarsly et al. |
| 2013/0105304 A1 | | 5/2013 | Kaczur et al. |
| 2013/0146448 A1 | | 6/2013 | Wang et al. |
| 2013/0175181 A1 | | 7/2013 | Kaczur et al. |
| 2013/0180865 A1 | | 7/2013 | Cole et al. |
| 2013/0199937 A1 | | 8/2013 | Cole et al. |
| 2014/0216934 A1 | | 8/2014 | Fu et al. |
| 2015/0171453 A1 | | 6/2015 | Chikashige et al. |
| 2015/0174570 A1 | | 6/2015 | Loveless et al. |
| 2015/0252482 A1 | | 9/2015 | Ono et al. |
| 2015/0345034 A1 | * | 12/2015 | Sundara ................ C25B 3/04 205/462 |
| 2016/0107154 A1 | | 4/2016 | Masel et al. |
| 2016/0108530 A1 | | 4/2016 | Masel et al. |
| 2016/0251766 A1 | | 9/2016 | Masel et al. |
| 2017/0128930 A1 | | 5/2017 | Masel et al. |
| 2017/0183789 A1 | * | 6/2017 | Matthews ............. C25B 13/08 |
| 2017/0189898 A1 | | 7/2017 | Masel et al. |
| 2017/0194633 A1 | | 7/2017 | Schumann et al. |
| 2017/0233881 A1 | | 8/2017 | Masel et al. |
| 2017/0263907 A1 | | 9/2017 | Ameyama et al. |
| 2018/0030187 A1 | | 2/2018 | Wang et al. |
| 2018/0127668 A1 | | 5/2018 | Masel |
| 2018/0316063 A1 | | 11/2018 | Masel et al. |

FOREIGN PATENT DOCUMENTS

| | | |
|---|---|---|
| KR | 101360269 B1 | 11/2012 |
| WO | 2008110830 A1 | 9/2008 |
| WO | 2016039999 A1 | 3/2015 |

OTHER PUBLICATIONS

Fisher et al., "Electrocatalytic Reduction of Carbon Dioxide by Using Macrocycles of Nickel and Cobalt", J. Am. Chem. Soc., vol. 102, No. 24 (1980), pp. 7361-7363.

Dewulf et al., "The electrochemical reduction of CO2 to CH4 and C2H4 at cu/nafion electrodes (solid polymer electrolyte structures)", Catalysis Letters 1 (1988), pp. 73-80.

Dubois et al., "Electrochemical Reduction of Carbon Dioxide Catalyzed by [Pd(Triphosphine)(Solvent)](BF4)2 Complexes: Synthetic and Mechanistic Studies", J. Am. Chem. Soc. 113 (1991), pp. 8753-8764.

Derien et al., "Activation of Carbon Dioxide: Nickel-Catalyzed Electrochemical Carboxylation of Diynes", J. Organic Chem. 58 (1993), pp. 2578-2588.

Ishida et al., "High-Temperature Electrochemical Reduction of Carbon Dioxide Using an Ionic Liquid". The Chem. Soc. of Jpn, Proceeding of 82th Autumn Meeting, Sep. 10, (2002), pp. 46, 1A6-01.

Kaneco et al., "Electrochemical conversion of carbon dioxide to methane in aqueous NaHCO3 solution at less than 273 K" Electrochimica Acta 48 (2002), pp. 51-55.

(56) References Cited

OTHER PUBLICATIONS

Lee et al., "Humidity-sensitive properties of new polyelectrolytes based on the copolymers containing phosphonium salt and phosphine function", J. Applied Polymer Science 89 (2003), pp. 1062-1070.
Tang et al., "Poly(ionic liquid)s as New Materials for CO2 Absorption", Journal of Polymer Science Part A: Polymer Chemistry 43 (2005), pp. 5477-5489.
Siroma et al., "Compact dynamic hydrogen electrode unit as a reference electrode for PEMFCs", J. of Power Sources 156 (2006), pp. 284-287.
Zhu et al., "Supported Choline Chloride/Urea as a Heterogeneous Catalyst for Chemical Fixation of Carbon Dioxide to cyclic Carbonates", Green Chem. 9 (2006), pp. 169-172.
Chen et al., "A Concept of Supported Amino Acid Ionic Liquids and Their Application in Metal Scavenging and Heterogeneous Catalysis", J. Am. Chem. Soc. 129 (2007), pp. 13879-13886.
Delacourt et al., "Design of an Electrochemical Cell Making Syngas (CO+H2) from CO2 and H2O Reduction at Room Temperature", J. of the Electrochemical Society 155 (2008), pp. B42-B49.
Fukuzumi, "Bioinspired Energy Conversion Systems for Hydrogen Production and Storage", Eur. J. Inorg. Chem. J008 (2008), pp. 1351-1362.
Wang et al., "Water-Retention Effect of Composite Membranes with Different Types of Nanometer Silicon Dioxide" Electrochemical and Solid State Letters 11 (2008), p. B201.
Yang et al., "Electrodeposition of Tin and Antimony in 1-Ethyl-3-Methylimidazolium Tetrafluoroborate Ionic Liquid", J. Appl. Electrochem 38 (2008), 537-542.
Barrosse-Antle et al., "Reduction of Carbon Dioxide in 1-Butyl-3-Methylimidazolium Acetate", Chem. Commun. (2009), pp. 3744-3746.
Luo et al., "Quaternized poly(methyl methacrylate-co-butyl acrylate-co-vinylbenzyl chloride) membrane for alkaline fuel cells", J. Power Sources. 195 (2010), pp. 3765-3771.
Tsutsumi et al., "A Test Method of a PEFC Single Cell with Reference Electrodes", Electrical Engineering in Japan, vol. 172, No. 1 (2010), pp. 1020-1026.
Li et al., "Novel anion exchange membranes based on polymerizable imidazolium salt for alkaline fuel cell applications", J. Mater. Chem. 21 (2011), pp. 11340-11346.
Narayanan et al., "Electrochemical Conversion of Carbon Dioxide to Formate in Alkaline Polymer Electrolyte Membrane Cells", J. of the Electrochemical Society 158 (2011), pp. A167-A173.
Rosen et al., "Ionic Liquid-Mediated Selective Conversion of CO2 to CO at Low Overpotentials", Science 334 (2011) pp. 643-644.
Weber et al., "Thermal and Ion Transport Properties of Hydrophilic and Hydrophobic Polymerized Styrenic Imidazolium Ionic Liquids", J. of Polymer Sci.: Part B: Polymer Phy. 49 (2011) pp. 1287-1296.
Sarode et al., "Designing Alkaline Exchange Membranes from Scratch", The Electrochemical Society, 220th ECS Meeting (2011).
Zhang et al., "Imidazolium functionalized polysulfone anion exchange membrane for fuel cell application", J. Mater. Chem. 21 (2011), pp. 12744-12752.
Aeshala et al., "Effect of solid polymer electrolyte on electrochemical reduction of CO2", Separation and Purification Technology 94 (2012), pp. 131-137.
Deavin et al., "Anion-Exchange Membranes for Alkaline Polymer Electrolyte Fuel Cells: Comparison of Pendent Benzyltrimethylammonium- and Benzylmethylimidazolium-Head-Groups", Energy Environ. Sci. 5 (2012), pp. 8584-8597.
Oh, "Synthesis and Applications of Imidazolium-Based Ionic Liquids and Their Polymer Derivatives", Dissertation at the Missouri University of Science and Technology (2012).
Qiu et al., "Alkaline Imidazolium- and Quaternary Ammonium-Functionalized Anion Exchange Membranes for Alkaline Fuel Cell Applications", J. Mater. Chem. 22 (2012), pp. 1040-1045.
Rosen et al., "In Situ Spectroscopic Examination of a Low Overpotential Pathway for Carbon Dioxide Conversion to Carbon Monoxide", J. of Physical Chemistry 116 (2012), pp. 15307-15312.

Aeshala et al., "Effect of cationic and anionic solid polymer electrolyte on direct electrochemical reduction of gaseous CO2 to fuel", Journal of CO2 Utilization 3-4 (2013), pp. 49-55.
Carmo et al., "A comprehensive review on PEM water electrolysis", International J. of Hydrogen Energy 38 (2013), pp. 4901-4934.
Chen et al., "Composite Blend Polymer Membrane with Increased Proton Selectivity and Lifetime for Vanadium Redox Flow Batteries", J. of Power Sources 231 (2013), pp. 301-306.
Genovese et al., "A gas-phase electrochemical reactor for carbon dioxide reduction back to liquid fuels", AIDIC Conference Series 11 (2013), pp. 151-160.
Hickner et al., "Anion Exchange Membranes: Current Status and Moving Forward", J. of Polymer Sci. 51 (2013), pp. 1727-1735.
Lin et al., "Alkaline Stable C2-Substituted Imidazolium-Based Anion-Exchange Membranes", Chem. Mater. 25 (2013), pp. 1858-1867.
Prakash et al., "Electrochemical reduction of CO2 over Sn-Nafion coated electrode for a fuel-cell-like device", J. of Power Sources 223 (2013), pp. 68-73.
Rosen et al., "Low temperature electrocatalytic reduction of carbon dioxide utilizing room temperature ionic liquids", Dissertation at the University of Illinois (2013).
Rosen et al., "Water Enhancement of CO2 Conversion on Silver in 1-Ethyl-3-Methylimidazolium Tetrafluoroborate", J. of the Electrochemical Society 160 (2013), pp. H138-H141.
Shironita et al., "Feasibility investigation of methanol generation by CO2 reduction using Pt/C-based membrane electrode assembly for a reversible fuel cell", J. of Power Sources 228 (2013), pp. 68-74.
Shironita et al., "Methanol generation by CO2 reduction at a PteRu/C electrocatalyst using a membrane electrode assembly", J. of Power Sources 240 (2013), pp. 404-410.
Thorson et al., "Effect of Cations on the Electrochemical Conversion of CO2 to CO", J. of the Electrochemical Society 160 (2013), pp. F69-F74.
Wu et al., "Electrochemical Reduction of Carbon Dioxide", J. of The Electrochemical Society 160 (2013), pp. F953-F957.
Aeshala et al., "Electrochemical conversion of CO2 to fuels: tuning of the reaction zone using suitable functional groups in a solid polymer electrolyte", Phys. Chem. Chem. Phys. 16 (2014), pp. 17588-17594.
Carlisle et al., "Vinyl-Functionalized Poly(imidazolium)s: A Curable Polymer Platform for Cross-Linked Ionic Liquid Gel Synthesis", Chem. Mater 26 (2014), pp. 1294-1296.
Ma et al., "Efficient Electrochemical Flow System with Improved Anode for the Conversion of CO2 to CO", J. of The Electrochemical Society 161 (2014), pp. F1124-F1131.
Parrondo et al., "Degradation of Anion Exchange Membranes Used for Hydrogen Production by Ultrapure Water Electrolysis", Royal Soc. of Chem. Adv. 4 (2014), pp. 9875-9879.
Said et al., "Functionalized Polysulfones as an Alternative Material to Improve Proton Conductivity at Low Relative Humidity Fuel Cell Applications", Chemistry and Materials Research 6 (2014), pp. 19-29.
Shi et al., "A novel electrolysis cell for CO2 reduction to CO in ionic liquid/organic solvent electrolyte", Journal of Power Sources 259 (2014) pp. 50-53.
Varcoe et al., "Anion-exchange membranes in electrochemical energy systems", Energy Environ. Sci. 7 (2014), pp. 3135-3191.
Yan et al., "Imidazolium-functionalized poly(ether ether ketone) as membrane and electrode ionomer for low-temperature alkaline membrane direct methanol fuel cell", Journal of Power Sources 250 (2014) pp. 90-97.
Kim et al., "Influence of dilute feed and pH on electrochemical reduction of CO2 to CO on Ag in a continuous flow electrolyzer", Electrochimica Acta 166 (2015), pp. 271-276.
Schauer et al., "Polysulfone-based anion exchange polymers for catalyst binders in alkaline electrolyzers", Journal of Applied Polymer Science (2015), pp. 1-7.
International Search Report and Written Opinion dated Jul. 6, 2015 in connection with International Application PCT/US2015/014328.
International Search Report and Written Opinion dated Jul. 20, 2015 in connection with International Application PCT/US2015/026507.

(56) References Cited

OTHER PUBLICATIONS

Korean Office Action dated Sep. 13, 2016 in connection with Korean Patent Application No. 10-2016-7022952.
Partial International Search Report dated Nov. 24, 2016 in connection with International Application PCT/US2016/045210.
International Search Report and Written Opinion dated Jan. 20, 2017 in connection with International Application PCT/US2016/045210.
International Preliminary Report on Patentability dated May 4, 2017 in connection with International Application PCT/US2015/026507.
International Preliminary Report on Patentability dated May 4, 2017 in connection with International Application No. PCT/US2015/014328.
Korean Office Action dated May 29, 2017 in connection with Korean Patent Application No. 10-2016-7022952.
Partial International Search Report dated Jun. 22, 2017 in connection with International Application PCT/US2017/025624.
Australian Office Action dated Jun. 29, 2017 in connection with Australian Patent Application No. 2015337093.
International Search Report and Written Opinion dated Jul. 12, 2017 in connection with International Application No. PCT/US2017/025628.
Office Action dated Sep. 13, 2017 in connection with Canadian Application No. 2,941,423.
International Search Report and Written Opinion dated Aug. 16, 2017 in connection with International Application No. PCT/US2017/025624.
Office Action dated Mar. 13, 2018 in connection with European Application No. 15722607.7.
Office Action dated May 23, 2018 in connection with Canadian Application No. 2,941,423.
Office Action dated Jun. 26, 2018 in connection with Australian Application No. 2015337093.
Chinese Office Action dated Dec. 24, 2018 in connection with Chinese App. No. 2015800151216.
Australian Office Action dated Jan. 23, 2019 in connection with Australian App. No. 2017246206.
Canadian Office Action dated Feb. 8, 2019 in connection with Canadian App. No. 2,941,423.
Komatsu et al., "Preparation of Cu-Solid Polymer Electrolyte Composite Electrodes and Application to Gas-Phase Electrochemical Reduction of CO2", Electrochimica Acta 40(6) (1995), pp. 745-753.
Sata et al., "Preparation and Properties of Anion Exchange Membranes Having Pyridinium or Pyridinium Derivatives as Anion Exchange Groups", Journal of Polymer Science Part A: Polymer Chemistry 36(1) (1998), pp. 49-58.
Torres et al., "Carbonate Species as OH-Carriers for Decreasing the pH Gradient between Cathode and Anode in Biological Fuel Cells" Env. Science & Tech. 42(23) (2008), pp. 8773-8777.
Marini et al., "Advanced alkaline water electrolysis", Electrochimica Acta (2012), pp. 384-391.
Ganesh, "Conversion of Carbon Dioxide into Methanol—a potential liquid fuel: Fundamental challenges and opportunities (a review)" Renewable and Sustainable Energy Reviews 31 (2014), pp. 221-257.
Pavel et al., "Highly Efficient Platinum Group Metal Free Based Membrane-Electrode Assembly for Anion Exchange Membrane Water Electrolysis", Angew. Chem. Int. Ed. 53 (2014), pp. 1378-1381.
Deng et al., "Linked Strategy for the Production of Fuels Via Formose Reaction", Sci. Reports 3 (2013), p. 1244.
Notice of Acceptance dated Feb. 21, 2019 in connection with Australian application No. 2017246207.
CA App. No. 2,941,423 Office Action dated Feb. 8, 2019 "CAOA0208".
CN App. No. 2015800151216 Office Action dated Dec. 24, 2018 "CNOA1224".
U.S. Appl. No. 15/810,106 Office Action dated Dec. 5, 2018 "USOA1205".
U.S. Appl. No. 16/024,827 Office Action dated Feb. 1, 2019 "USOA0201".
AU App. No. 2017246206 Office Action dated Jan. 23, 2019 "AUOA0123".
U.S. Appl. No. 15/922,883 Office Action dated Jan. 30, 2019 "USOA0130".
U.S. Appl. No. 16/164,289 Office Action dated Feb. 1, 2019 "USOA0201b".
PCT/US2015/014328 filed on Feb. 3, 2015 International Search Report and Written Opinion dated Jul. 6, 2015 ("20150706ISR") International Preliminary Report on Patentability dated May 4, 2017 ("20170504IPRPa").
CA App. No. 2,941,423 filed on Apr. 17, 2015 Office Action dated Sep. 13, 2017 ("20170903CAOA").
PCT/US2015/026507 filed on Apr. 17, 2015 International Search Report and Written Opinion dated Jul. 20, 2015 ("20150720ISR") International Preliminary Report on Patentability dated May 4, 2017 ("20170504IPRPb").
U.S. Appl. No. 14/704,934, filed May 5, 2015 Office Action dated Dec. 1, 2015 ("20151201USOA") Office Action dated Apr. 27, 2016 ("20160427USOA").
U.S. Appl. No. 14/704,935, filed May 5, 2015 Office Action dated Oct. 26, 2015 ("20151026USOA").
PCT/US2016/045210 filed on Aug. 2, 2016 Partial International Search Report dated Nov. 24, 2016 ("20161124PISR") International Search Report and Written Opinion dated Jan. 20, 2017 ("20170120ISR").
KR App. No. 10-2016-7022952 filed on Aug. 23, 2016 Korean Office Action dated Sep. 13, 2016 ("20160913KROA") Korean Office Action dated May 29, 2017 ("20170529KROA").
U.S. Appl. No. 15/158,227, filed May 18, 2016 Office Action dated Mar. 22, 2017 ("20170322USOA") Office Action dated Sep. 22, 2017 ("20170922USOA").
EP App. No. 15722607.7 filed Sep. 1, 2016 Office Action dated Mar. 13, 2018 ("20180313EPOA").
U.S. Appl. No. 15/260,213, filed Sep. 8, 2016 Office Action dated Sep. 1, 2017 ("20170901USOA") Office Action dated Jan. 29, 2018 ("20180129USOA").
U.S. Appl. No. 15/400,775, filed Jan. 6, 2017 Office Action dated May 26, 2017 ("20170526USOA").
PCT/US2017/025624 filed on Mar. 31, 2017 Partial International Search Report dated Jun. 22, 2017 ("20170622PISR") International Search Report and Written Opinion dated Aug. 16, 2017 ("20170816ISR").
PCT/US2017/025628 filed on Mar. 21, 2017 International Search Report and Written Opinion dated Jul. 12, 2017 ("20170712ISR").
AU App. No. 2015337093 filed on May 21, 2017 Australian Office Action dated Jun. 29, 2017 ("20170629AUOA").
AU App. No. 2015337093 filed Aug. 3, 2016 Office Action dated Jun. 26, 2018 ("20180626AUOA").
CA App. No. 2,941,423 filed Aug. 31, 2016 Office Action dated May 23, 2018 ("20180523CAOA").
U.S. Appl. No. 15/684,548, filed Aug. 23, 2017 Office Action dated Jun. 6, 2018 ("20180606USOA").
U.S. Appl. No. 15/724,933, filed Oct. 4, 2017 Office Action dated Jun. 6, 2018 ("20180606USOAb") Office Action dated Aug. 6, 2018 ("20180806USOA").
U.S. Appl. No. 15/810,106, filed Nov. 12, 2017 Office Action dated Jun. 21, 2018 ("20180621USOA").
European Office Action dated Mar. 27, 2019 in connection with European App. No. 11713569.9.
Seshadri et al., "A New Homogeneous Electrocatalyst for the Reduction of Carbon Dioxide to Methanol at Low Overpotential", J. Electroanalytical Chem. 372 (1994), pp. 145-150.

\* cited by examiner

CATALYST LAYERS AND ELECTROLYZERS

CROSS-REFERENCE TO RELATED APPLICATIONS

The present application is a divisional of U.S. non-provisional patent application Ser. No. 15/258,227 filed on May 18, 2016, entitled "Catalyst Layers and Electrolyzers", now U.S. Pat. No. 9,945,040 issued on Apr. 17, 2018. The '227 application is a continuation-in-part of and claims priority benefits from U.S. non-provisional patent application Ser. No. 14/704,935 filed on May 5, 2015, entitled "Ion-Conducting Membranes", now U.S. Pat. No. 9,370,773 issued on Jun. 21, 2016. The '935 non-provisional application is a continuation-in-part of International Application No. PCT/US2015/14328, filed on Feb. 3, 2015, entitled "Electrolyzer and Membranes". The '328 international application claimed priority benefits, in turn, from U.S. provisional patent application Ser. No. 62/066,823, filed on Oct. 21, 2014. The '935 non-provisional application is also a continuation-in-part of International Application No. PCT/US2015/26507, filed on Apr. 17, 2015, entitled "Electrolyzer and Membranes". The '507 international application also claimed priority benefits from the '823 provisional application.

The '227 application is also related to and claims priority benefits from U.S. provisional patent application Ser. No. 62/066,823, filed on Oct. 21, 2014.

The '227 application is also a continuation-in-part of and claims priority benefits from U.S. non-provisional patent application Ser. No. 14/704,934, filed on May 5, 2015, entitled "Electrochemical Device For Converting Carbon Dioxide To A Reaction Product", now U.S. Pat. No. 9,481,939 issued on Nov. 1, 2016. The '934 non-provisional application is a continuation-in-part of the '328 international application. The '328 international application claimed priority benefits, in turn, from the '823 provisional application. The '934 non-provisional application is also a continuation-in-part of the '507 international application. The '507 international application also claimed priority benefits from the '823 provisional application.

The '227 application is also a continuation-in part of the '507 international application and is also a continuation-in-part of the '328 international application.

The '227 application is also a continuation-in-part of and claims priority benefits from U.S. non-provisional patent application Ser. No. 15/090,477, filed on Apr. 4, 2016, entitled "Ion-Conducting Membranes", now U.S. Pat. No. 9,580,824 issued on Feb. 28, 2017. The '477 application is also a continuation-in-part of the '935 application.

The '823 provisional application, the '477, '934 and '935 non-provisional applications, and the '328 and '507 international applications are each hereby incorporated by reference herein in their entirety.

This application is also related to U.S. patent application Ser. No. 14/035,935, filed on Sep. 24, 2013, entitled "Devices and Processes for Carbon Dioxide Conversion into Useful Fuels and Chemicals," now U.S. Pat. No. 9,181,625 issued on Nov. 10, 2015; U.S. patent application Ser. No. 12/830,338, filed on Jul. 4, 2010, entitled "Novel Catalyst Mixtures", now abandoned; International Application No. PCT/2011/030098 filed on Mar. 25, 2011, entitled "Novel Catalyst Mixtures"; U.S. patent application Ser. No. 13/174,365, filed Jun. 30, 2011, entitled "Novel Catalyst Mixtures"; International Patent Application No. PCT/US2011/042809, filed Jul. 1, 2011, entitled "Novel Catalyst Mixtures"; U.S. patent application Ser. No. 13/530,058, filed Jun. 21, 2012, entitled "Sensors for Carbon Dioxide and Other End Uses"; International Patent Application No. PCT/US2012/043651, filed Jun. 22, 2012, entitled "Low Cost Carbon Dioxide Sensors"; and U.S. patent application Ser. No. 13/445,887, filed Apr. 12, 2012, entitled "Electrocatalysts for Carbon Dioxide Conversion," now issued as U.S. Pat. No. 9,012,345 issued on Apr. 21, 2015.

STATEMENT OF GOVERNMENT INTEREST

This invention was made, at least in part, with U.S. government support under ARPA-E Contracts No. DE-AR-0000345, and DE-AR0000684. The government has certain rights in the invention.

FIELD OF THE INVENTION

The field of the invention is electrochemistry. The devices, systems and compositions described involve the electrochemical conversion of carbon dioxide into useful products, the electrolysis of water, electric power generation using fuel cells and electrochemical water purification.

BACKGROUND OF THE INVENTION

There is a desire to decrease carbon dioxide ($CO_2$) emissions from industrial facilities and power plants as a way of reducing global warming and protecting the environment. One solution, known as carbon sequestration, involves the capture and storage of $CO_2$. Often the $CO_2$ is simply buried. It would be valuable if instead of simply burying or storing the $CO_2$, it could be converted into another product and put to a beneficial use.

Over the years, a number of electrochemical processes have been suggested for the conversion of $CO_2$ into useful products. Some of these processes and their related catalysts are discussed in U.S. Pat. Nos. 3,959,094; 4,240,882; 4,349,464; 4,523,981; 4,545,872; 4,595,465; 4,608,132; 4,608,133; 4,609,440; 4,609,441; 4,609,451; 4,620,906; 4,668,349; 4,673,473; 4,711,708; 4,756,807; 4,818,353; 5,064,733; 5,284,563; 5,382,332; 5,457,079; 5,709,789; 5,928,806; 5,952,540; 6,024,855; 6,660,680; 6,664,207; 6,987,134; 7,157,404; 7,378,561; 7,479,570; U.S. Patent App. Pub. No. 2008/0223727; Hori, Y., "Electrochemical CO2 reduction on metal electrodes", *Modern Aspects of Electrochemistry* 42 (2008), pages 89-189; Gattrell, M. et al. "A review of the aqueous electrochemical reduction of CO2 to hydrocarbons at copper", *Journal of Electroanalytical Chemistry* 594 (2006), pages 1-19; and DuBois, D., *Encyclopedia of Electrochemistry*, 7a, Springer (2006), pages 202-225.

Processes utilizing electrochemical cells for chemical conversions have been known for years. Generally, an electrochemical cell contains an anode, a cathode and an electrolyte. Catalysts can be placed on the anode, the cathode, and/or in the electrolyte to promote the desired chemical reactions. During operation, reactants or a solution containing reactants are fed into the cell. In an electrolytic cell, voltage is then applied between the anode and the cathode to promote the desired electrochemical reaction. Note that the convention for designating the cathode and anode is that the cathode is the electrode at which chemical reduction occurs. This is different for electrolytic cells (also known as electrolyzers, devices in which electrical energy is supplied in order to force a chemical oxidation-reduction reaction) than for galvanic cells (such as fuel cells and batteries) in which a spontaneous electrochemical reaction produces electricity in an external circuit during normal operation. In either case, a chemical species acquires electrons from the cathode, thus becoming more negative and reducing its formal oxidation number.

When an electrochemical cell is used as a $CO_2$ conversion system, a reactant comprising $CO_2$, carbonate or bicarbonate is fed into the cell. A voltage is applied to the cell, and the $CO_2$ reacts to form new chemical compounds.

One of the issues at present is that to obtain high currents, one needs to run the electrochemical cells for conversion of $CO_2$ either at low voltage efficiency or with continuous additions of co-reactants. For example, Schmidt et al., Electrochemical Reduction of $CO_2$ (available at http://www.sccer-hae.ch/resources/Talks/08_Krause_Power_to_Value.pdf; last accessed on May 17, 2016) report that over 6 volts need to be applied to achieve a current of 600 $mA/cm^2$. This corresponds to an electrical efficiency of 21%. Verma, S. et al. Phys. Chem. Chem. Phys., 2016. 18: p. 7075-7084 find that they can achieve 400 $mA/cm^2$ at a cell potential of 3 V (42% electrical efficiency) by continuously supplying 3 M KOH to the cell. Unfortunately, if the KOH is recycled, the KOH will react with $CO_2$ to form $KHCO_3$. Verma et al. find that the current drops to 40 $mA/cm^2$ in $KHCO_3$.

An electrochemical cell for the conversion of $CO_2$ that achieves (a) reasonable energy efficiencies (at least 40%), (b) reasonable currents (above 150 $mA/cm^2$), and (c) reasonable selectivities (above 50%), without needing to continuously introduce other reactants, would represent a significant advance in the electrochemical field.

SUMMARY OF THE INVENTION

In one embodiment, an electrolyzer cathode catalyst layer allows high currents to be obtained at lower voltages. The catalyst layer contains one or more catalytically active chemical elements and an anion conducting polymer, wherein the ion conducting polymer is comprised of positively charged cyclic amine groups.

Preferably the cyclic amine is a one or more of imidazoliums, pyridiniums, pyrazoliums, pyrrolidiniums, pyrroliums, pyrimidiums, piperidiniums, indoliums, triaziniums, and polymers thereof; more preferably the polymer is one or more of imidazoliums, pyridiniums and pyrazoliums.

Preferably said pyridiniums have no hydrogens directly bound to the nitrogen.

Preferably said imidazoliums, pyrazoliums, pyrrolidiniums, pyrroliums, pyrimidiums, piperidiniums, indoliums, triaziniums, have at least one nitrogen that has no hydrogens directly bound to it.

Preferably such positive charged cyclic amine groups are aromatic.

Preferably the catalytic chemical element is chosen from the list: V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Tl, Pb, Bi, Sb, Te, U, Sm, Tb, La, Ce, and Nd; more preferably the catalytically active element is chosen from the list Pt, Pd, Au, Ag, Cu, Ni, Fe, Sn, Bi, Co, In, Ru and Rh; most preferably the catalytically active element is chosen from the list Au, Ag, Cu, Sn, Sb, Bi, and In.

In a preferred embodiment, the weight of the ion conducting polymer in the catalyst layer is less than 64% of the weight of the catalytically active element. Most preferably the weight of the ion conducting polymer in the catalyst layer is between 1 and 10% of the weight of the catalytically active element.

In a preferred embodiment the catalyst layer also contains elemental carbon, most preferably carbon black, such as that available from Cabot Corporation, Boston, Mass., USA, under the trade designation Vulcan XC-72R.

The catalyst layer can be part of an electrolyzer, fuel cell, battery or sensor.

In a preferred embodiment the catalyst layer is part of an electrolyzer. Electrolysis products may include CO, $OH^-$, $HCO^-$, $H_2CO$, $(HCO_2)^-$, HCOOH, $H_2O_2$, $CH_3OH$, $CH_4$, $C_2H_4$, $CH_3CH_2OH$, $CH_3COO^-$, $CH_3COOH$, $C_2H_6$, $O_2$, $H_2$, $(COOH)_2$, and $(COO^-)_2$.

The feed to the electrolyzer may include at least one of $CO_2$, $HCO_3^-$, $CO_3^{2-}$ and $H_2O$.

The catalyst layer may be in electrical contact with the anode or cathode.

In one embodiment, the catalyst layer is part of a $CO_2$ electrolyzer. Preferably $CO_2$ is fed into the electrolyzer cathode and water is fed into the anode.

In a preferred embodiment, the water feed contains an electrolyte, preferably a carbonate, bicarbonate or hydroxide.

DETAILED DESCRIPTION OF ILLUSTRATIVE EMBODIMENTS

Figure 1:
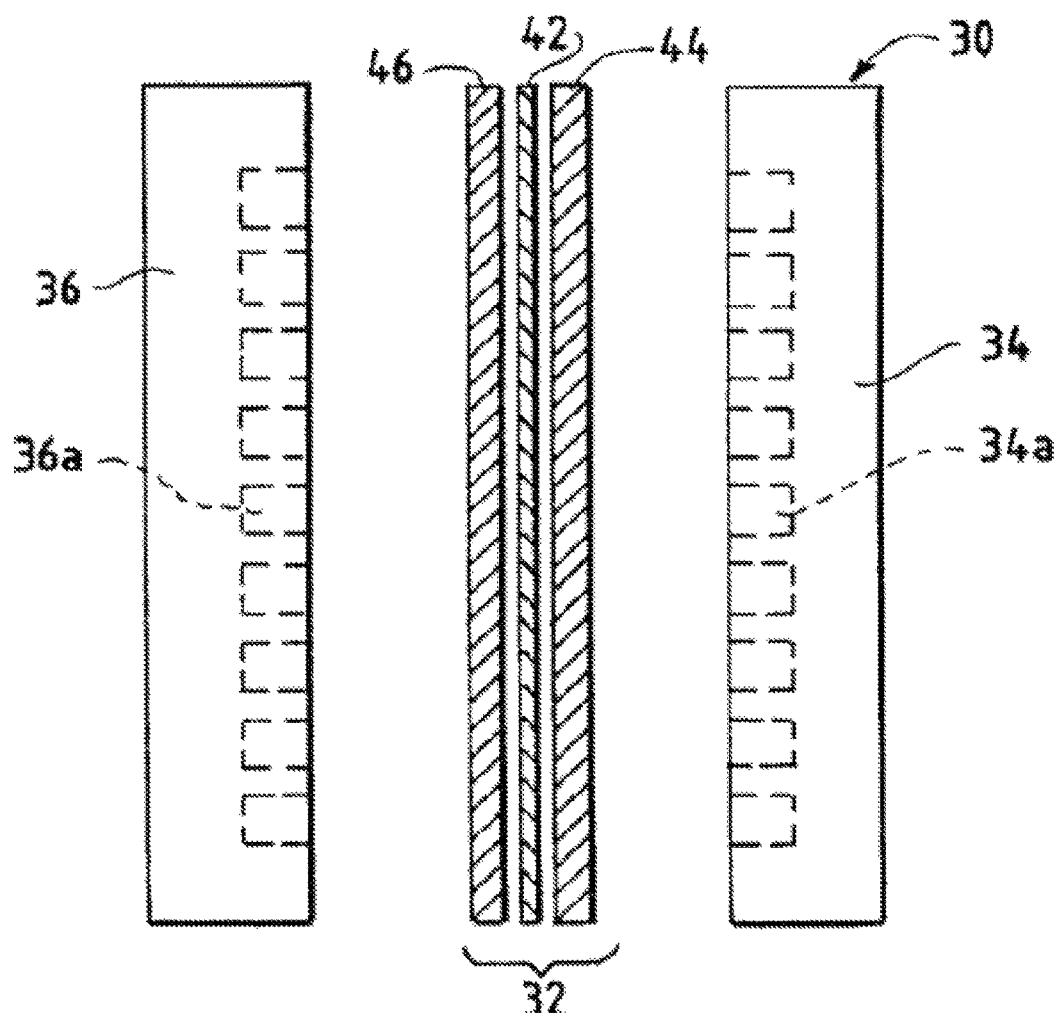
FIG. 1 is an exploded side view of a fuel cell hardware assembly including a membrane electrode assembly interposed between two fluid flow field plates having reactant flow channels formed in the major surfaces of the plates facing the electrodes.

It is understood that the process is not limited to the particular methodology, protocols and reagents described herein, as these can vary as persons familiar with the technology involved here will recognize. It is also to be understood that the terminology used herein is used for the purpose of describing particular embodiments only, and is not intended to limit the scope of the process. It also is to be noted that as used herein and in the appended claims, the singular forms "a," "an," and "the" include the plural reference unless the context clearly dictates otherwise. Thus, for example, a reference to "a linker" is a reference to one or more linkers and equivalents thereof known to those skilled in the art. Similarly, the phrase "and/or" is used to indicate one or both stated cases can occur, for example, A and/or B includes (A and B) and (A or B).

Unless defined otherwise, technical and scientific terms used herein have the same meanings as commonly understood by one of ordinary skill in the art to which the process pertains. The embodiments of the process and the various features and advantageous details thereof are explained more fully with reference to the non-limiting embodiments and/or illustrated in the accompanying drawings and detailed in the following description. It should be noted that the features illustrated in the drawings are not necessarily drawn to scale, and features of one embodiment can be employed with other embodiments as the skilled artisan would recognize, even if not explicitly stated herein.

Any numerical value ranges recited herein include all values from the lower value to the upper value in increments of one unit, provided that there is a separation of at least two units between any lower value and any higher value. As an example, if it is stated that the concentration of a component or value of a process variable such as, for example, size, angle, pressure, time and the like, is, for example, from 1 to 98, specifically from 20 to 80, more specifically from 30 to 70, it is intended that values such as 15 to 85, 22 to 68, 43 to 51, 30 to 32, and the like, are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value are to be treated in a similar manner.

Moreover, provided immediately below is a "Definitions" section, where certain terms related to the articles and process are defined specifically. Particular methods, devices, and materials are described, although any methods and materials similar or equivalent to those described herein can be used in the practice or testing of the process or articles.

Definitions

The term "electrochemical conversion of $CO_2$" as used here refers to any electrochemical process where carbon dioxide, carbonate, or bicarbonate is converted into another chemical substance in any step of the process.

The term polymer electrolyte membrane refers to both cation exchange membranes, which generally comprise polymers having multiple covalently attached negatively charged groups, and anion exchange membranes, which generally comprise polymers having multiple covalently attached positively charged groups. Typical cation exchange membranes include proton conducting membranes, such as the perfluorosulfonic acid polymer available under the trade designation NAFION from E. I. du Pont de Nemours and Company (DuPont) of Wilmington, Del.

The term anion exchange polymer refers to polymers having multiple covalently attached positively charged groups.

The term "anion exchange membrane electrolyzer" as used here refers to an electrolyzer with an anion-conducting polymer electrolyte membrane separating the anode from the cathode.

The term "Hydrogen Evolution Reaction" also called "HER" as used here refers to the electrochemical reaction $2H^+ + 2e^- \rightarrow H_2$.

The term "MEA" as used here refers to a membrane electrode assembly, which typically comprises at least an ion-conducting membrane having an anode layer attached or in close proximity to one face of the membrane and a cathode layer attached or in close proximity to the other side of the membrane.

The Term "CV" refers to cyclic voltammetry or cyclic voltammogram.

The term "Millipore water" is water that is produced by a Millipore filtration system with a resistivity of at least 18.2 megohm-cm.

The term "GC" as used here refers to a gas chromatograph.

The term "imidazolium" as used here refers to a positively charged ligand containing an imidazole group. This includes a bare imidazole or a substituted imidazole. Ligands of the form:

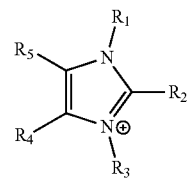

where $R_1$-$R_5$ are each independently selected from hydrogen, halogens, linear alkyls, branched alkyls, cyclic alkyls, heteroalkyls, aryls, cyclic aryls, heteroaryls, alkylaryls, heteroalkylaryls, and polymers thereof, such as the vinyl benzyl copolymers described herein, are specifically included.

The term "pyridinium" as used here refers to a positively charged ligand containing a pyridinium group. This includes a protonated bare pyridine or a substituted pyridine or pyridinium. Ligands of the form

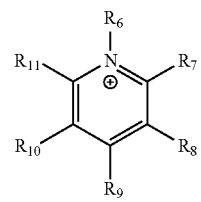

where $R_6$-$R_{11}$ are each independently selected from hydrogen, halogens, linear alkyls, branched alkyls, cyclic alkyls, heteroalkyls, aryls, cyclic aryls, heteroaryls, alkylaryls, heteroalkylaryls, and polymers thereof, such as the vinyl benzyl copolymers described herein, are specifically included.

The term "pyrazoliums" as used here refers to a positively charged ligand containing a pyrazolium group. This includes a bare pyrazolium or a substituted pyrazolium. Ligands of the form

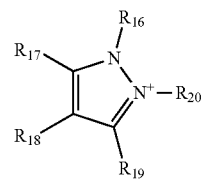

where $R_{16}$-$R_{20}$ are each independently selected from hydrogen, halogens, linear alkyls, branched alkyls, cyclic alkyls, heteroalkyls, aryls, cyclic aryls, heteroaryls, alkylaryls, heteroalkylaryls, and polymers thereof, such as the vinyl benzyl copolymers described herein, are specifically included.

The term "phosphonium" as used here refers to a positively charged ligand containing phosphorous. This includes substituted phosphorous. Ligands of the form:

$$P^+(R_{12}R_{13}R_{14}R_{15})$$

where $R_{12}$-$R_{15}$ are each independently selected from hydrogen, halogens, linear alkyls, branched alkyls, cyclic alkyls, heteroalkyls, aryls, cyclic aryls, heteroaryls, alkylaryls, heteroalkylaryls, and polymers thereof, such as the vinyl benzyl copolymers described herein, are specifically included.

The term "positively charged cyclic amine" as used here refers to a positively charged ligand containing a cyclic amine. This specifically includes imidazoliums, pyridiniums, pyrazoliums, pyrrolidiniums, pyrroliums, pyrimidiums, piperidiniums, indoliums, triaziniums, and polymers thereof, such as the vinyl benzyl copolymers described herein.

The term "electrochemical device" as used here refers to a device capable of either generating electrical energy from chemical reactions or facilitating chemical reactions through the introduction of electrical energy. Batteries, fuel cells, electrolyzers, and electrochemical reactors are specifically included.

The term "vinyl benzyl derivatives" as used here refers to a chemical of the form.

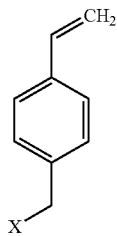

or polymers thereof where X is hydrogen, halogens, linear alkyls, branched alkyls, cyclic alkyls, heteroalkyls, aryls, cyclic aryls, heteroaryls, alkylaryls, heteroalkylaryls, imidazoliums, pyridiniums, pyrazoliums, pyrrolidiniums, pyrroliums, pyrimidiums, piperidiniums, indoliums, or triaziniums. Polymers thereof, such as the vinyl benzyl copolymers described herein, are specifically included.

Specific Description

One embodiment of the advance is an electrolyzer cathode catalyst layer that improves the output of a $CO_2$ electrolyzer.

FIG. 1 illustrates a fuel cell hardware assembly 30, which includes a membrane electrode assembly 32 interposed between rigid flow field plates 34 and 36, the flow fields typically being formed of graphite or a graphite composite material. Flow field channels 34a are formed in the surface of flow field plate 34 facing membrane electrode assembly 32. Flow field channels 36a are formed in the surface of flow field plate 36 facing membrane electrode assembly 32. Membrane electrode assembly 32 consists of a polymer electrolyte (ion exchange) membrane 42 interposed between two electrodes, namely, anode 44 and cathode 46. Anode 44 and cathode 46 are typically formed of porous electrically conductive sheet material, preferably carbon fiber paper, and have planar major surfaces. Electrodes 44 and 46 have a thin layer of catalyst material disposed on their major surfaces at the interface with membrane 42 to render them electrochemically active.

A distinguishing feature here is the addition of anion conducting polymers to the catalyst layer to improve the cell output.

There are many previous descriptions of catalyst layers for electrochemical cells. Patents include U.S. Pat. Nos. 5,234,777; 5,869,416; 6,156,449; 6,696,382; 6,800,391; 6,844,286; 7,364,813; 7,754,369; 7,754,369; 7,855,160; 7,906,452; 8,198,206; 8,481,231; 8,940,460; 9,127,182; and 9,160,008; U.S. Pat. App. Pub. Nos. 2002/0034674; 2002/0098405; 2004/0023104; 2004/0107869; 2005/0151121; 2006/0110631; 2008/0248944; 2010/0196785; 2010/0285951; 2011/0003071; 2011/0166009; 2011/0262828; 2012/0094210; 2012/0148936; 2012/0171583. 2012/0196741; 20120/258381; 2013/0260278; 2014/0162170; 2014/0220474; and 2014/0228200; and International Publication Nos. WO2015/092371 and WO2015/124250. However, in most cases acidic polymers such as perfluorosulfonic acids, including those available from DuPont under the trade designation Nafion, are used. Acidic polymers substantially decrease the selectivity of $CO_2$ electrolyzers, so they are typically not useful in practical $CO_2$ electrolyzers.

Figure 2:
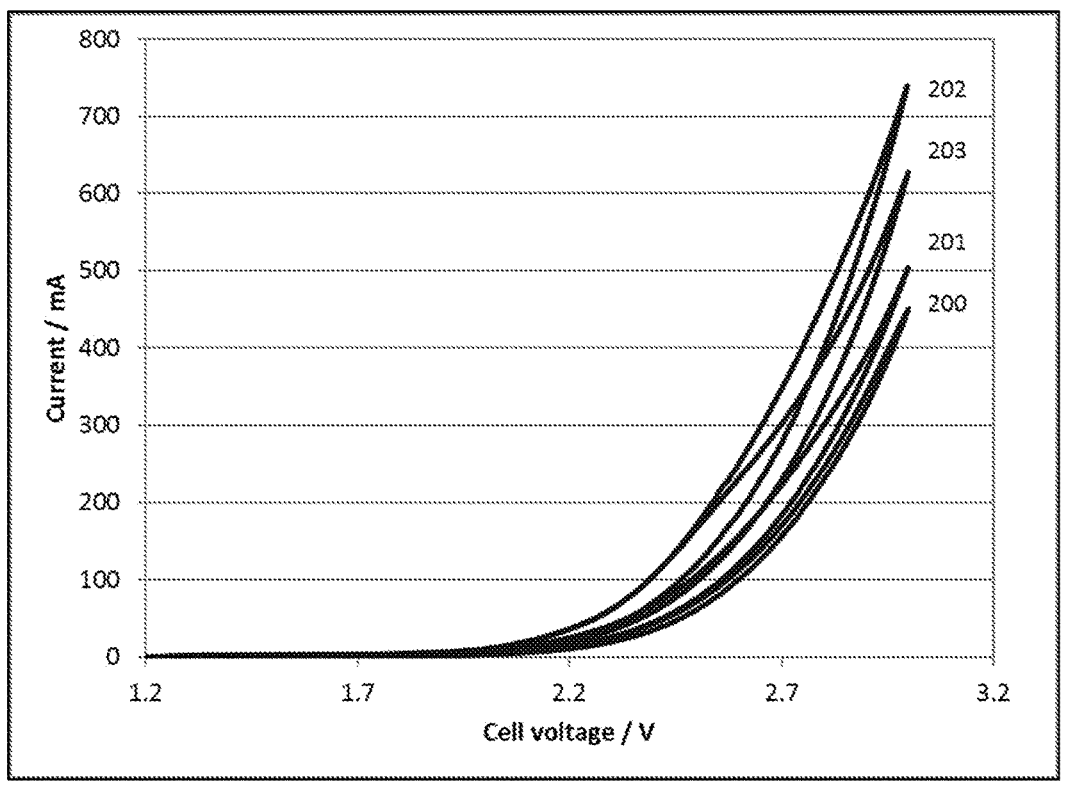
FIG. 2 shows how the voltammograms of a 5 $cm^2$ cell change when 0% (200), 1% (201), 5% (202), and 10% (203) of PSMIMCl are added to the $CO_2$ electrolyzer cathode catalyst layer, where the percentage is calculated as the weight of the PSMIMCl divided by the weight of the silver.

There are a few reports of anionic fuel cells with anion conducting polymers having multiple covalently attached positively charged groups in their catalyst layer. See for example U.S. Pat. Nos. 3,403,054; 7,785,750; and 8,257,872; U.S. Pat. App. Pub. No. 20150171453; International Publication Nos. WO/2013/0137011 and WO/2012/078513; and Matsuoka et al., Journal of Power Sources, Volume 150, 4 Oct. 2005, pages 27-31. However, these authors use polymers containing amines of the form:

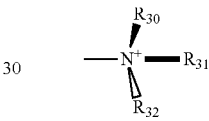

where the bond on the left is an attachment to the polymer and the R groups are either, hydrogens, methyls or ethyls, not positively charged cyclic amines such as imidazolium or pyrazolium. Si et al. (J. Mater. Chem. A, 2014. 2: p. 4413-4421), Yan et al (J. Power Sources, 2014. 250: p. 90-97), and Schauer et al. (the Schauer paper) Journal of Applied Polymer Science, 2015. 132: 42581, disclose imidazole functionalized poly(arylene ether sulfone) and poly(ether ketone) polymers, but Schauer et al. FIG. 2 shows that these polymers are unstable under alkaline conditions so they are unsuitable for use in alkaline electrolyzers.

U.S. Pat. No. 6,841,285, notes that, "Thus imidazole and pyrazole may act as both hydrogen donors and acceptors in proton conduction processes. While these compounds may show increased conductivity within membrane systems, it is unlikely that they are suitable for use within the fuel cell environment. For example, a recent study by C. Yang et al., Journal of Power Sources 103:1, 2001, reports that imidazole impregnated membranes poisoned the catalysts."

Note that imidazole and pyrazole would be protonated under the acidic conditions in U.S. Pat. No. 6,841,285 thus forming imidazolium and pyrazolium ions, so that the implication of the '285 patent is that imidazoliums and pyrazoliums should not be used in a catalyst layer.

The present work shows that in contrast to the implication in the '285 patent, polymers containing imidazoliums, pyrazoliums and pyridiniums enhance the performance of a $CO_2$ electrolyzer.

The catalyst layer can also include at least one Catalytically Active Element. "Catalytically Active Element" as used here refers to a chemical element that can serve as a catalyst for the electrochemical conversion of $CO_2$ or another species of interest in a desired reaction. In particular, the device can include one or more of the following Catalytically Active Elements: V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Tl, Pb, Bi, Sb, Te, U, Sm, Tb, La, Ce, and Nd. Research has established that Pt, Pd, Au, Ag, Cu, Ni, Fe, Sn, Bi, Co, In, Ru and Rh perform well, with Au, Ag, Cu, Sn, Sb, Bi, and In perform especially well.

Embodiments of the present invention also include the addition of electrically conductive species to the catalyst layer, with carbon being a conductive preferred component.

Without further elaboration, it is believed that persons familiar with the technology involved here using the preceding description can utilize the invention to the fullest extent. The following examples are illustrative only, and are not meant to be an exhaustive list of all possible embodiments, applications or modifications of the invention.

Specific Example 1

The objective of this example is to show that in contrast to the indication in U.S. Pat. No. 6,841,285, the addition of polymers containing imidazoliums to the catalyst layer enhances the performance of a $CO_2$ electrolyzer.

A copolymer, which is designated here as PSMIM (Cl), was prepared following the synthetic route in patent application Ser. No. 14/704,935. "PSMIM" refers to a co-polymer of polystyrene and poly 1-(p-vinylbenzyl)-3-methylimidazolium:

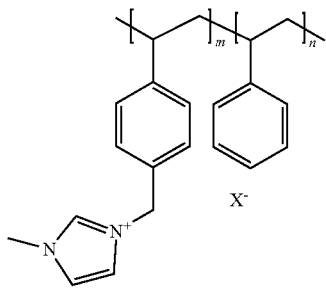

where $X^-$ is an anion, m>0 and n>0.

The inhibitor-free styrene was prepared by passing styrene (Sigma-Aldrich, Saint Louis, Mo.) through the tert-butylcatechol (TBC) inhibitor remover (Sigma-Aldrich 311340). In general, 40 ml of remover is sufficient to yield 50 ml of clear, inhibitor free styrene. Inhibitor TBC in 4-vinylbenzyl chloride (4-VBC) was removed by the same inhibitor remover in a similar fashion.

Poly(4-vinylbenzyl chloride-co-styrene) was then synthesized by heating a solution of inhibitor-free styrene (Sigma-Aldrich) (36.139 g, 350 mmol) and 4-vinylbenzyl chloride (Sigma-Aldrich) (29.7272 g, 190 mmol) in chlorobenzene (Sigma-Aldrich) (45 ml) at 60-65° C. in an oil bath for approximately 20 hours under argon gas with AIBN (α,α'-Azoisobutyronitrile, Sigma-Aldrich) (0.5927 g, 0.90 wt % based on the total monomers' weight) as initiator. The copolymer was precipitated in $CH_3OH$ (methanol) and dried under vacuum.

"Polystyrene methyimidazolium chloride" (PSMIM) was synthesized by adding 1-methylimidazole (Sigma-Aldrich) (2.8650 g, 034.9 mmol), which is an alkylimidazole, to the solution of the poly(4-VBC-co-St) (5.0034 g, 19.4 mmol) in anhydrous N,N-Dimethylformamide (DMF) (Sigma-Aldrich) (30 mL). The mixture was then stirred at around 30° C. for around 50 hours to form a PSMIM solution.

"4-VBC-co-St" or "poly(4-vinylbenzyl chloride co-styrene)" as used here refers to a co-polymer of styrene and 4-vinylbenzyl chloride:

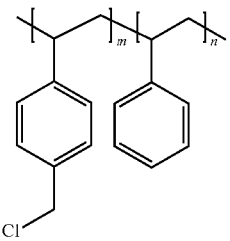

PSMIM-DVB was synthesized starting with poly(4-vinylbenzyl chloride co-styrene.) 1-methylimidazole (Sigma-Aldrich) (3.912 g, 47.7 mmol) was added in a 250 ml 3-neck round bottom flask to the solution of the poly(4-VBC-co-St) (15.358 g, 59.8 mmol) in anhydrous N,N-Dimethylformamide (DMF) (Sigma-Aldrich) (105 mL). 0.22 ml of a divinylbenzene (DVB) in DMF solution (DVB concentration=0.0083 g/ml) was carefully added through a pipette to the mixture with continual magnetic stirring. After this, 0.22 ml of AIBN-DMF solution (AIBN concentration=0.0083 g/ml) was added to the mixture in a similar fashion. The reaction was then kept under nitrogen atmosphere at 50° C. for about 60 hours. PSMIM-DVB was obtained as a white powder after purification by precipitation into diethyl ether.

Membranes were prepared by casting the PSMIM-DVB solution prepared above directly onto a flat glass surface. The thickness of the solution on the glass was controlled by a film applicator (MTI Corporation, Richmond, Calif.) with an adjustable doctor blade. The membranes were then dried in a vacuum oven in the following step wise fashion. They were first kept at 80° C. for 120 minutes, then at 100° C. for 60 minutes, at 120° C. for 30 minutes and finally at 150° C. for 60 minutes. Chloride ions in the membranes were removed by soaking the membranes in 1 M KOH solution for 24 hours or longer.

The cathode layer in Specific Example 1 was prepared as follows. Silver ink was made by mixing 100 mg of silver nanoparticles (20-40 nm, 45509, Alfa Aesar, Ward Hill, Mass.), 5 mg porous carbon (Vulcan XC-72R, Fuel Cell Earth, Woburn, Mass.) and different amounts of PSMIM-Cl in 3 ml of ethanol (459844, Sigma-Aldrich, St. Louis, Mo.). The mixture was then sonicated for 10 minutes. The silver ink was painted onto a gas diffusion layer (Sigracet 35 BC GDL, Ion Power Inc., New Castle, Del.) covering an area of 6 cm×6 cm. The electrode was immersed in 1 M KOH for at least 1 hour so that PSMIM-Cl converted by ion exchange to PSMIM-OH. Then the electrode was cut into 2.5 cm×2.5 cm sections for cell testing.

The anode in Specific Example 1 was prepared as follows: 100 mg of $IrO_2$ (43396, Alfa Aesar, Ward Hill, Mass.) was dispersed in the mixture of 1 ml of deionized water, 2 ml of isopropanol (3032-16, Macron Fine Chemicals, Avantor Performance Materials, Center Valley, Pa.) and 0.1 ml of 5 wt. % poly-tetrafluoroethylene (PTFE) dispersion (665800, Sigma-Aldrich, St. Louis, Mo.). The mixture was sonicated for 10 min using a water bath sonicator. The ink was painted onto 6 cm×6 cm of carbon fiber paper (Toray Paper 120, Fuel Cell Earth, Woburn, Mass.). The actual $IrO_2$ loading was about 2 mg/$cm^2$. The electrode was cut into 3 cm×3 cm sections for cell testing.

The membrane was sandwiched between the anode and the cathode with the metal-containing layers on the anode and cathode facing the membrane, and the whole assembly was mounted in a Fuel Cell Technologies 5 cm² fuel cell hardware assembly with serpentine flow fields.

$CO_2$ humidified at 25° C. was fed into the cathode flow field at a rate of 20 sccm, and 10 mM $KHCO_3$ was fed into the anode flow field. The cyclic voltammograms were collected by scanning the cell potential from 1.2 to 3.0 V. All of the scans were made at room temperature and atmospheric pressure.

FIG. 2 shows the results. Plot 200 is a base case with no PSMIM in the cathode catalyst layer ink. Notice that the current increases when PSMIM is added to the catalyst layer in a later sample, such that the PSMIM weight is 1% of the weight of the silver (plot 201). Further increases in the current are seen as the PSMIM concentration is increased so that the PSMIM weight is 5% of the weight of the silver (plot 202). Then there is a small decrease when the weight of the PSMIM is increased to 10% of the weight of the silver (plot 203). A decrease in the selectivity of the reaction was observed.

A run in which the PSMIM weight was 20% of the weight of the silver was also performed. The cell showed a small current, but analysis of the exit stream did not show significant $CO_2$ conversion.

These results demonstrate that the addition of an ionomer containing an imidazolium enhances the performance of a $CO_2$ electrolyzer, in contrast to the findings in U.S. Pat. No. 6,841,285.

Specific Example 2

The objective of this example is to show that in contrast to the findings in U.S. Pat. No. 6,841,285, the addition of polymers containing tetra-methyl-imidazolium to the catalyst layer enhances the performance of a $CO_2$ electrolyzer.

Preparation of PSTMIM: poly(4-vinylbenzyl chloride-co-styrene) was prepared as in Specific Example 1. Tetra-methyl-imidazolium (TCI) (5.934 g) was added to the solution of the poly(4-VBC-co-St) (10 g) in anhydrous N,N-Dimethylformamide (DMF) (Sigma-Aldrich) (85 mL). The mixture was stirred at 30-35° C. for around 60 hours. PSTMIM was obtained as white solid particles after purification by precipitation into diethyl ether. PSTMIM refers to a material that contains a co-polymer of styrene and 1-(p-vinylbenzyl)-tetra-methyl-imidazolium.

The cathode in Specific Example 2 was prepared as follows. Silver ink was made by mixing 100 mg of silver nanoparticles (20-40 nm, 45509, Alfa Aesar, Ward Hill, Mass.), 5 mg porous carbon (Vulcan XC-72R, Fuel Cell Earth, Woburn, Mass.) and different amounts of PSTMIM-Cl in 3 ml of ethanol (459844, Sigma-Aldrich, St. Louis, Mo.). The mixture was then sonicated for 10 minutes. The silver ink was painted onto a gas diffusion layer (Sigracet 35 BC GDL, Ion Power Inc., New Castle, Del.) covering an area of 6 cm×6 cm. The electrode was immersed in 1 M KOH for at least 1 hour so that PSTMIM-Cl converted to PSTMIM-OH. Then the electrode was cut into 2.5 cm×2.5 cm for cell testing.

The anode in specific example 2 was the same as in Specific Example 1 and the cell was tested as in Specific Example 1.

Figure 3:
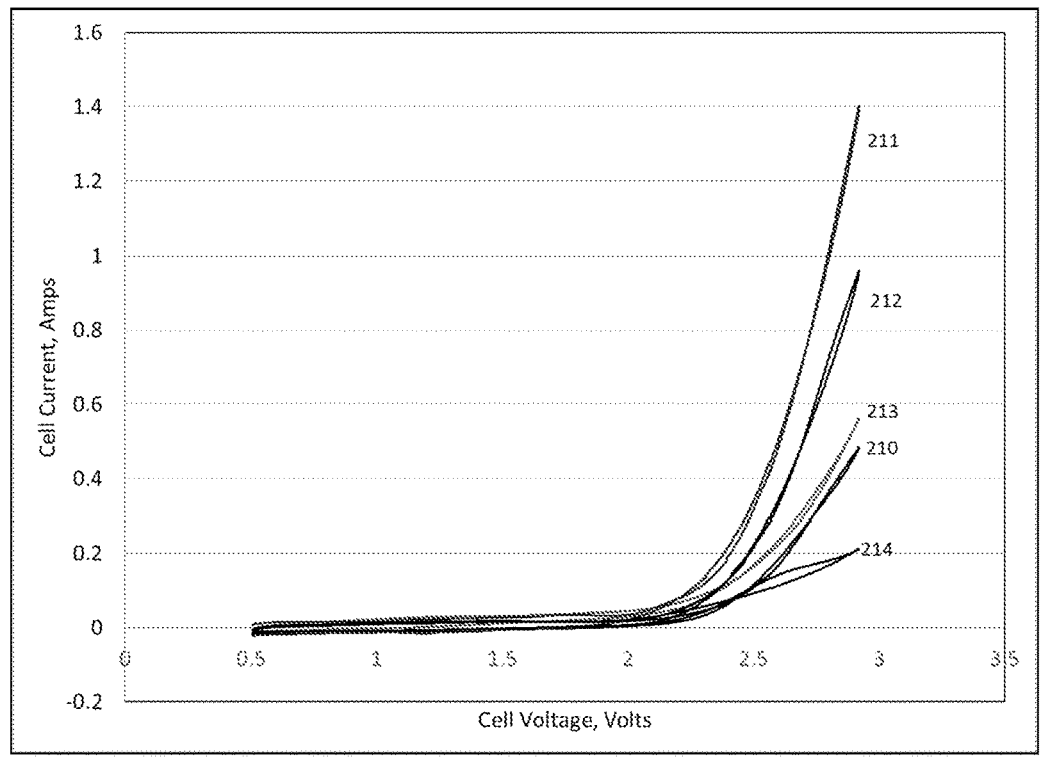
FIG. 3 shows how the voltammograms of a 5 $cm^2$ $CO_2$ electrolyzer cell change when 1% (210), 4% (211), 8% (212), 16% (213) and 32% (214) of PSTMIMCl are added to the cathode catalyst layer.

FIG. 3 shows the voltammograms measured at varying PSTMIM content. Notice that the current is higher than the base case (plot 200) in FIG. 2 when PSTMIM is added to the catalyst later so that the PSTMIM weight is 1% of the weight of the silver (plot 210). Further increases in the current are seen as the PSTMIM concentration is increased so that the PSTMIM weight is 4% of the weight of the silver (plot 211). Then there is a small decrease when the weight of the PSTMIM is increased to 8% of the weight of the silver (plot 212). The performance continues to decrease when the weight of the PSTMIM is 16% of the weight of the silver (plot 213), but the cell current is still higher than the base case in FIG. 2 (plot 200). The performance is lower than the base case in FIG. 2 (plot 200) when the weight of the PSTMIM is 32% of the weight of the silver (plot 214), but the cell current is still significant.

A run in which the PSTMIM weight was 64% of the weight of the silver was also performed. The cell showed a small current, but analysis of the exit stream did not show significant $CO_2$ conversion. These results demonstrate that the addition of an ionomer containing tetra-methyl-imidazolium enhances the performance of a $CO_2$ electrolyzer, in contrast to the findings in the '285 patent.

Specific Example 3

The objective of this example is to show that in contrast to the findings in U.S. Pat. No. 6,841,285, the addition of polymers containing pyridiniums to the catalyst layer changes the performance of a $CO_2$ electrolyzer but does not poison it.

Preparation of PSMP: poly(4-vinylbenzyl chloride co-styrene) was prepared as in Specific Example 1. Pyridine (Sigma-Aldrich) (0.318 g, 4.68 mmol) was added to the solution of the poly(4-VBC-co-St) (1 g, 3.89 mmol) in anhydrous N,N-Dimethylformamide (DMF) (Sigma-Aldrich) (8 mL). The mixture was stirred at room temperature for 60 hours, and PSMP was obtained as a white solid after purification by precipitation into diethyl ether. PSMP refers to a material that contains a co-polymer of styrene and 1-(p-vinylbenzyl)-pyridinium.

The cathode in Specific Example 3 was prepared as follows. Silver ink was made by mixing 100 mg of silver nanoparticles (20-40 nm, 45509, Alfa Aesar, Ward Hill, Mass.), 5 mg porous carbon (Vulcan XC-72R, Fuel Cell Earth, Woburn, Mass.) and different amounts of PSMP-Cl in 3 ml of ethanol (459844, Sigma-Aldrich, St. Louis, Mo.). The mixture was then sonicated for 10 minutes. The silver ink was painted onto a gas diffusion layer (Sigracet 35 BC GDL, Ion Power Inc., New Castle, Del.) covering an area of 6 cm×6 cm. The electrode was immersed in 1 M KOH for at least 1 hour so that PSMP-Cl was converted to PSMP-OH. Then the electrode was cut into 2.5 cm×2.5 cm sections for cell testing.

The anode in Specific Example 3 was the same as in Specific Example 1 and the cell was tested as in Specific Example 1.

Figure 4:
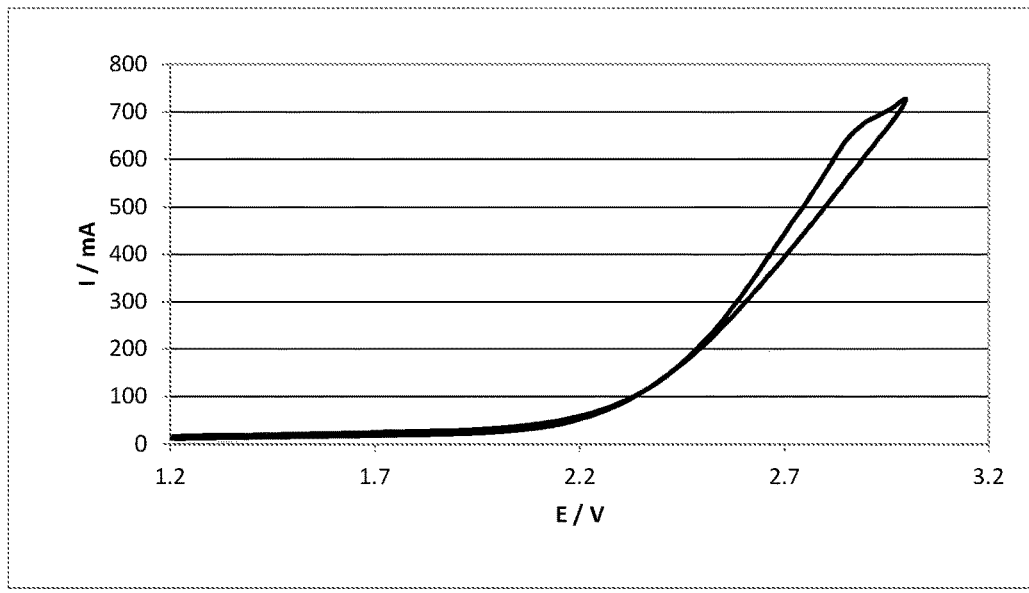
FIG. 4 shows how the voltammograms of a 5 $cm^2$ $CO_2$ electrolyzer cell change when 5x% PSMP is added to the cathode catalyst layer.

FIG. 4 shows the voltammograms measured when the weight of the PSMP was 5% of the weight of the silver. Notice that the current is considerably above the base case (200) in FIG. 2. These results demonstrate that the addition of an ionomer containing a pyridinium enhances the performance of a $CO_2$ electrolyzer, in contrast to the findings in the '285 patent.

Specific Example 4

The objective of this example is to show that in contrast to the findings in the '285 patent, the addition of polymers containing pyrazoliums to the catalyst layer enhances the performance of a $CO_2$ electrolyzer.

Preparation of PSPZ: poly(4-vinylbenzyl chloride co-styrene) was prepared as in Specific Example 1. Pyrazole (Sigma-Aldrich) (0.593 g, 4.67 mmol) was added to the solution of the poly(4-VBC-co-St) (1 g, 3.89 mmol) in anhydrous N,N-Dimethylformamide (DMF) (Sigma-Aldrich) (8 mL). The mixture was stirred at room temperature for 60 hours and this PSPY-DMF was accordingly further diluted for use as the ionomer. PSPY refers to a material that contains a co-polymer of styrene and 1-(p-vinylbenzyl)-pyrazolium ionomers.

The anode in Specific Example 4 was the same as in Specific Example 1 and the cell was tested as in Specific Example 1.

Figure 5:
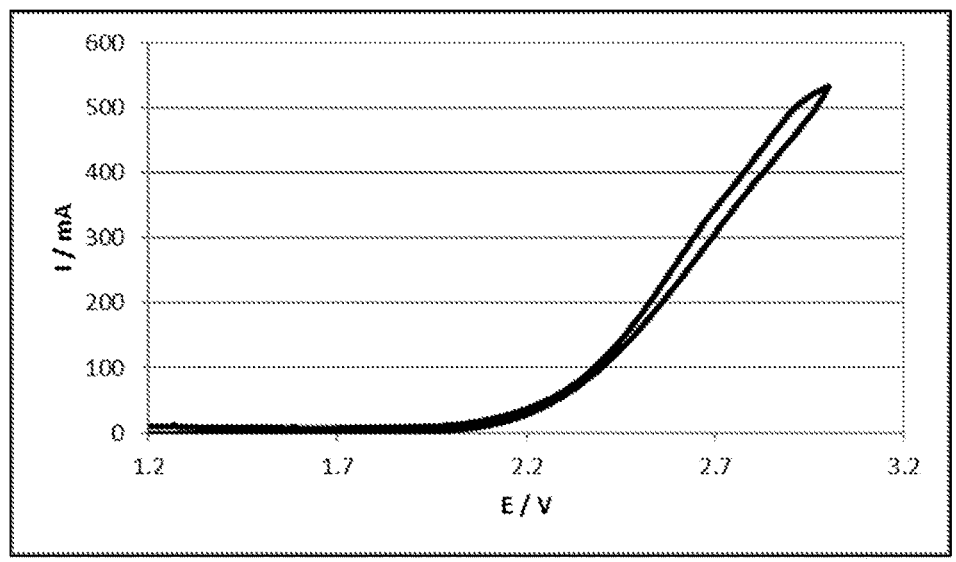
FIG. 5 shows how the voltammograms of a 5 $cm^2$ $CO_2$ electrolyzer cell change when 5% of PSPY is added to the cathode catalyst layer.

FIG. 5 shows a voltammogram measured when the weight of the PSPY was 5% of the weight of the silver. Notice that the current is considerably above the base case (200) in FIG. 2. These results demonstrate that the addition of an ionomer containing a pyrazolium enhances the performance of a $CO_2$ electrolyzer, in contrast to the findings in the '285 patent.

Specific Example 5

The objective of this example is to show that the addition of a PSMIM to the cathode of a $CO_2$ electrolyzer also improves the steady state performance of the electrolyzer.

The anode and cathode for this test were synthesized as in Specific Example 1. The weight of the PSMIM in the cathode layer was 2% of the weight of the silver.

A PSTMIM-DVB membrane was used in this experiment. The preparation of the PSTMIM-DVB membrane is as follows: Poly(4-vinylbenzyl chloride co-styrene) was formed as in specific example 1. Tetramethylimidazole (TMIM) (TCI) (4.05 g, 32.6 mmol) was added in a 250 ml 3-neck round bottom flask to the solution of the poly(4-VBC-co-St) (10 g, 38.9 mol) in anhydrous N,N-Dimethyl-formamide (DMF) (Sigma-Aldrich) (73 mL). After the TMIM was thoroughly dissolved within this reaction mixture, 1 mL of a DVB-DMF solution (DVB concentration=0.052 g/ml) was carefully added through a pipette to the mixture with continual magnetic stirring. After this, 1 ml of AIBN-DMF solution (AIBN concentration=0.00135 g/ml) was added to the mixture in a similar fashion. The reaction was then kept under nitrogen atmosphere at 50° C. for about 60 hours. PSTMIM was obtained as a white powder after purification by precipitation into diethyl ether. A PSTMIM-DVB membrane was then formed as in Specific Example 1.

The cell was assembled and tested as in Specific Example 1.

Figure 6:
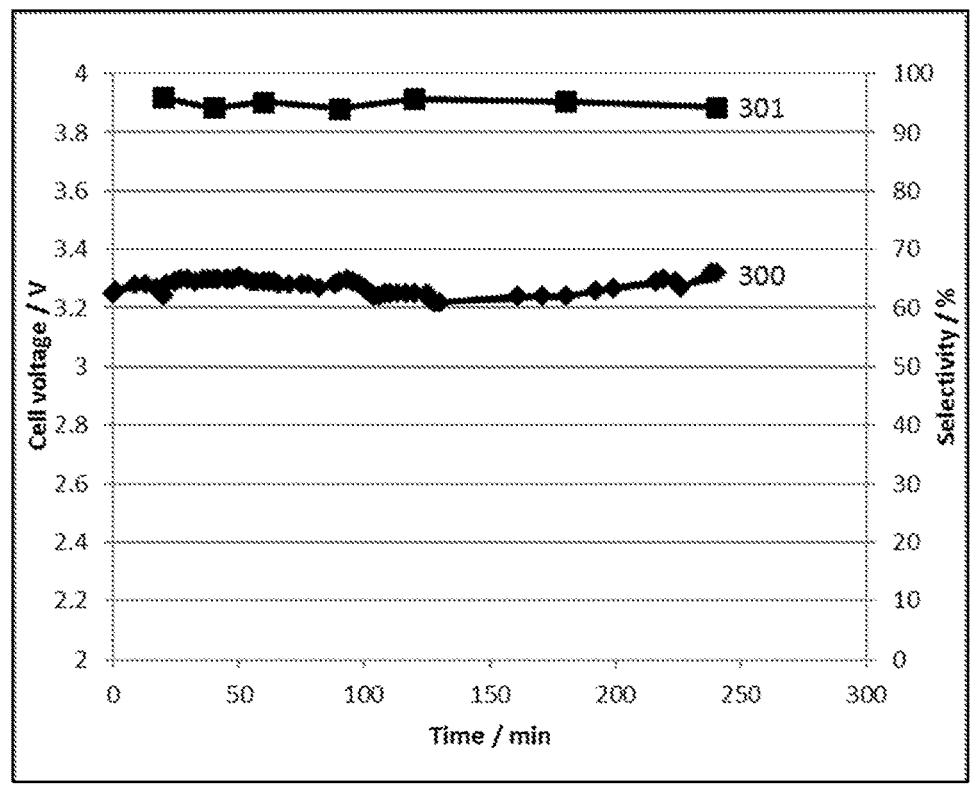
FIG. 6. Shows how the voltage (300) and selectivity (301) of a 5 $cm^2$ $CO_2$ electrolyzer varies with time when the cell is run at a constant current of 600 $mA/cm^2$.

FIG. 6 shows how the voltage and selectivity varied with time when the cell was held at a fixed current of 3 amps (600 mA/cm$^2$). Notice that the cell is producing 600 mA/cm$^2$ at 3.3 volts. GC analysis showed that the cell was converting $CO_2$ to CO with over 95% selectivity to CO. By comparison, the Schmidt paper (referred to above, available at http://www.sccer-hae.ch/resources/Talks/08_Krause_Power_to_Value.pdf; last accessed on May 17, 2016) requires over 6 volts to reach the same current. Consequently, our cell would only need about half as much energy as Schmidt et al.'s to convert $CO_2$ at a rate corresponding to 600 mA/cm$^2$. The results are stable. The loss of performance reported in the Schauer paper is not seen.

More generally, notice that Specific Examples 1, 2, 3, 4 and 5 show that adding three different ion conducting polymer containing positively charged cyclic amine groups to the catalyst layer in a $CO_2$ electrolyzer enhance the performance of a $CO_2$ electrolyzer, in contrast to the findings in the '285 patent. This observation is believed to be general. That is, adding ion conducting polymer containing positively charged cyclic amine groups can enhance the performance of electrolyzers and other devices.

While particular elements, embodiments and applications of the present invention have been shown and described, it will be understood that the invention is not limited thereto since modifications can be made by those skilled in the art without departing from the scope of the present disclosure, particularly in light of the foregoing teachings.

The examples given above are merely illustrative and are not meant to be an exhaustive list of all possible embodiments, applications or modifications of the present electrochemical device. Thus, various modifications and variations of the described articles, methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the chemical arts or in the relevant fields are intended to be within the scope of the appended claims.

What is claimed is:

1. A catalyst layer for an electrochemical device comprising a catalytically active element and an ion conducting polymer wherein said ion conducting polymer comprises:
   (a) positively charged cyclic amine groups; and
   (b) polymers or copolymers of styrene, and wherein the weight of the ion conducting polymer in the catalyst layer is less than 64% of the weight of the catalytically active element.

2. The catalyst layer of claim 1, wherein said ion conducting polymer comprises one or more of imidazoliums, pyridiniums, pyrazoliums, pyrrolidiniums, pyrroliums, pyrimidiums, piperidiniums, indoliums, or triaziniums.

3. The catalyst layer of claim 2, wherein said ion conducting polymer comprises one or more of imidazoliums, pyridiniums, or pyrazoliums.

4. The catalyst layer of claim 2, wherein said catalytically active element comprises one or more of V, Cr, Mn, Fe, Co, Ni, Cu, Sn, Zr, Nb, Mo, Ru, Rh, Pd, Ag, Cd, Hf, Ta, W, Re, Ir, Pt, Au, Hg, Al, Si, In, Tl, Pb, Bi, Sb, Te, U, Sm, Tb, La, Ce or Nd.

5. The catalyst layer of claim 4, wherein said catalytically active element comprises one or more of Pt, Pd, Au, Ag, Cu, Ni, Fe, Sn, Bi, Co, In, Ru or Rh.

6. The catalyst layer of claim 5, wherein said catalytically active element comprises one or more of Au, Ag, Cu, Sn, Sb, Bi or In.

7. The catalyst layer of claim 6, wherein the weight of the ion conducting polymer in the catalyst layer is less than 64% of the weight of the catalytically active element in the catalyst layer.

8. The catalyst layer of claim 7, wherein the weight of the ion conducting polymer is at least 1% and less than or equal to 10% of the weight of the catalytically active element in the catalyst layer.

9. The catalyst layer of claim 1, wherein said catalyst layer also comprises elemental carbon.

10. The catalyst layer of claim 9, wherein the carbon is a carbon black.

11. The catalyst layer of claim 1, wherein the electrochemical device is an electrolyzer.

12. The catalyst layer of claim 11, wherein operation of the electrolyzer produces electrolysis products comprising one or more of $CO$, $OH^-$, $HCO^-$, $H_2CO$, $HCO_2^-$, $HCOOH$, $H_2O_2$, $CH_3OH$, $CH_4$, $C_2H_4$, $CH_3CH_2OH$, $CH_3COO$, $CH_3COOH$, $C_2H_6$, $O_2$, $H_2$, $(COOH)_2$ or $(COO)_2$.

13. An electrochemical device comprising the catalyst layer of claim 1, wherein the electrochemical device is a sensor.

14. An electrochemical device comprising the catalyst layer of claim 1, wherein the device is a fuel cell.

* * * * *